United States Patent
Middleton et al.

(10) Patent No.: US 10,690,573 B2
(45) Date of Patent: Jun. 23, 2020

(54) METHODS OF REDUCING VISCOSITY OF BIOLOGICAL SAMPLES

(71) Applicant: Cytoskeleton, Inc., Denver, CO (US)

(72) Inventors: Kim Middleton, Denver, CO (US); Soonjin Hong, Denver, CO (US); Wai K. Law, Denver, CO (US); Henrick Horita, Denver, CO (US)

(73) Assignee: Cytoskeleton, Inc., Denver, CO (US)

( * ) Notice: Subject to any disclaimer, the term of this patent is extended or adjusted under 35 U.S.C. 154(b) by 65 days.

(21) Appl. No.: 15/604,809

(22) Filed: May 25, 2017

(65) Prior Publication Data
US 2017/0343455 A1    Nov. 30, 2017

Related U.S. Application Data

(60) Provisional application No. 62/341,236, filed on May 25, 2016, provisional application No. 62/359,834, filed on Jul. 8, 2016.

(51) Int. Cl.
*G01N 1/40* (2006.01)
*G01N 1/38* (2006.01)
*G01N 33/543* (2006.01)
*G01N 33/68* (2006.01)

(52) U.S. Cl.
CPC ............. *G01N 1/4077* (2013.01); *G01N 1/38* (2013.01); *G01N 33/54313* (2013.01); *G01N 33/6872* (2013.01); *G01N 2001/386* (2013.01); *G01N 2001/4088* (2013.01); *G01N 2333/70596* (2013.01); *G01N 2440/36* (2013.01)

(58) Field of Classification Search
None
See application file for complete search history.

(56) References Cited

U.S. PATENT DOCUMENTS

| 10,077,308 B2 * | 9/2018 | Wang ................. C07K 16/2827 |
| 10,166,273 B2 * | 1/2019 | Wittrup ............. A61K 38/2013 |
| 2012/0053328 A1 | 3/2012 | Yan et al. |

OTHER PUBLICATIONS

Karwacz et al. (OncoImmunology 2012 1:86-88 (Year: 2012).*
Kulpa et al. (Seminars in Immunology 2012 25: 219-227 (Year: 2013).*
Boynton et al., "Reduction of cell lysate viscosity during processing of poly(3-hydroxyalkanoates) by chromosomal integration of the staphylococcal nuclease gene in Pseudomonas putida", Applied & Env Microbiol, 1999, 65, p. 1524-1529.
Moser et al., "Optimization of immunoprecipitation—western blot analysis in detecting GW182-associated components of GW/P bodies", Nat Protoc, 2009, 4, p. 674-685.

* cited by examiner

*Primary Examiner* — Changhwa J Cheu
(74) *Attorney, Agent, or Firm* — Stradley Ronon Stevens & Young, LLP

(57) ABSTRACT

The present disclosure provides methods for reducing the viscosity of a cell lysate or tissue lysate by: contacting the cell lysate or tissue lysate with a compressible and open-cell foam filter having a pore size from about 0.65 mm to about 1.22 mm, compressing the filter to recover the lysate absorbed in the filter, and collecting the filtered lysate; and also provides kits therefor.

15 Claims, 10 Drawing Sheets

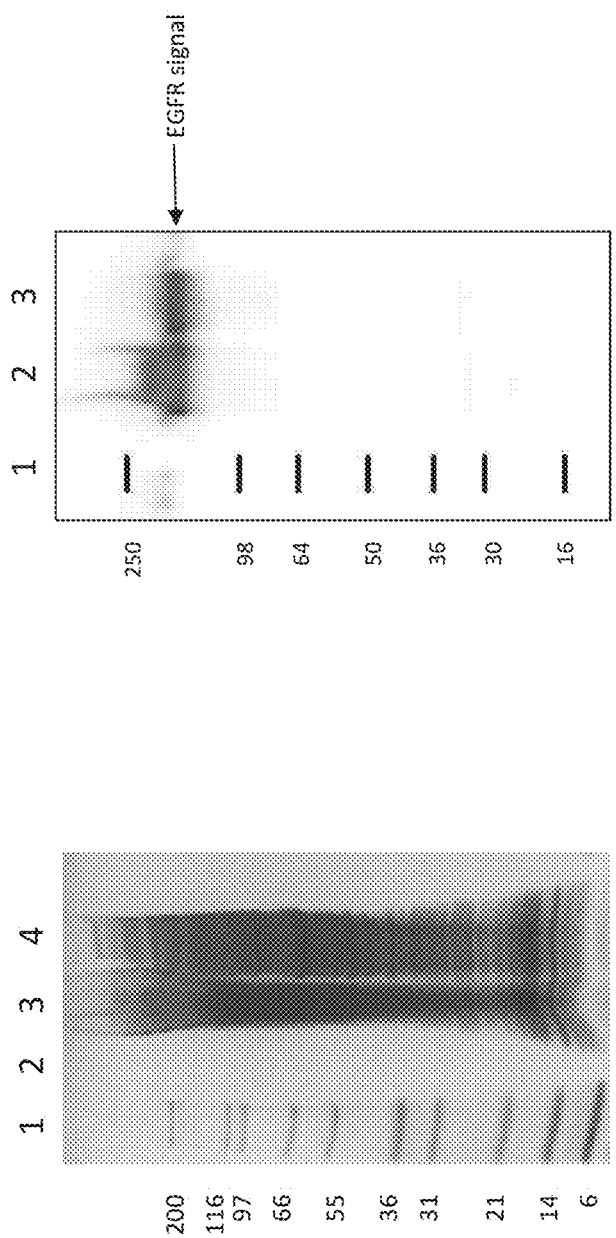

| Property | Working Range | Optimal Value |
|---|---|---|
| Pore size | 0.65 ~ 1.22 mm | 0.7mm |
| Density | 1.3 ~ 3.0 lbs/ft^3 | 1.4 |
| Indentation Load Deflection (ILD) or Indentation Force Deflection (IFD) | 60~90 IFD | 70 |

Figure 9

METHODS OF REDUCING VISCOSITY OF BIOLOGICAL SAMPLES

CROSS-REFERENCE TO RELATED APPLICATIONS

This application claims priority to U.S. provisional application Ser. No. 62/341,236 filed May 25, 2016, and to U.S. provisional application Ser. No. 62/359,834 filed Jul. 8, 2016, each of which is incorporated herein by reference in its entirety.

FIELD

The present disclosure is directed, in part, to methods for reducing the viscosity of cell or tissue lysates, and kits therefore.

BACKGROUND

Analysis and purification of polypeptides from biological samples often involves the lysis of a cell or tissue sample as a precursor to downstream polypeptide processing. It is well recognized that genomic DNA is often released during cell or tissue lysis and that this causes an increased viscosity of the lysate that can interfere with downstream polypeptide analysis or purification. Common biotechnical methods that require or benefit from reduction in lysate viscosity include:

1) Western blot analysis. For example, Chen et al., Front. Biosci., 2014, 4, 2365-2377 describes the process of reducing lysate viscosity by several pulses of sonication for the preparation of lysates destined for Western blot analysis (see, Section 3.5. Sample preparation).

2) Immunoprecipitations. For example, Moser et al., Nat. Protoc., 2009, 4, 674-685 describes the critical nature of reducing lysate viscosity by passing four times through a syringe fitted with a 21 G 1.5 inch needle. It is also noted that the gauge of the needle is critical to successful lysis, viscosity reduction and immunoprecipitation step (see, Procedure step 7).

3) Laboratory and industrial scale protein purification. For example, Maine et al., Nat. Protoc., 2010, 5, 1447-1459 states that "proper sonication is mandatory because otherwise the high viscosity of the lysate will prevent it from being handled through the initial precipitation" (see, Procedure, Step 10 p. 1452). Another example can be found in DeWalt et al., Protein Expression & Purification, 2003, 28, 220-223 describes a method of reducing a microbial lysate viscosity by utilizing a polycationic compaction agent such as spermidine to facilitate the downstream purification of a His-tagged protein from the treated lysate.

Many methods have been devised that remove or shear genomic DNA and thereby reduce lysate viscosity to allow for more efficient downstream processing of lysate polypeptides. One method is sonication (see, Maine et al., supra), which effectively breaks up genomic DNA but can often result in partial or total denaturation of the target protein. Another method is passage of the lysate through a fine gauge needle (see, Moser et al., supra). This method is very time consuming and tedious and does not scale well to larger lysate volumes. Yet another method includes treatment of lysates with a compaction agent (see, DeWalt et al., supra). Yet another method involves treating the lysate with nucleases such as Benzonase® (see, U.S. Pat. No. 5,173,418). Several methods have been reported that use a filter system to reduce viscosity of a cell or tissue lysate. For example U.S. Patent Application Publication No. 2012/0053328 reports a filter system that retains genomic DNA while allowing polypeptides to be collected in the filtrate. This is a relatively rapid and gentle method, however the fact that it requires the use of specialized equipment such as a centrifuge or a vacuum limits its usefulness. Chromosomal integration of nuclease genes into protein expression systems have been used to reduce viscosity (see, Boynton et al., Applied & Env. Microbiol., 1999, 65, 1524-1529). In addition, treatment of lysates with exogenous nucleases, sonication of lysates (see, Methods in enzymology Ed. J. Lorsch. 2015. Strep-tagged protein purification. vol. 559 chapter 5 p. 61) have also been used to reduce viscosity of lysates.

Methods for rapid, gentle, and one-step removal of genomic DNA and cellular debris from crude cell and tissue lysates that does not require the use of specialized equipment while allowing for collection of cellular polypeptides from, for example, viscous cell lysates is desired.

SUMMARY

The present disclosure provides methods for reducing the viscosity of a cell lysate or tissue lysate comprising: a) contacting the cell lysate or tissue lysate with a compressible and open-cell foam filter having a pore size from about 0.65 mm to about 1.22 mm, wherein the filter is present in a syringe; b) compressing the filter to recover the lysate absorbed in the filter, wherein the compression ratio is from about 50% to about 95%; and collecting the filtered lysate, wherein the filtered lysate contains at least 95% of the polypeptides in the original unfiltered cell lysate or original unfiltered tissue lysate, and wherein the filtered lysate contains no more than 10% of the genomic DNA in the original unfiltered cell lysate or original unfiltered tissue lysate. In some embodiments, the foam filter has a density from about 1.3 lbs/ft$^3$ to about 3.0 lbs/ft$^3$. In some embodiments, the foam filter has an Indentation Load Deflection (ILD), also referred to as Indentation Force Deflection (IFD), from about 60 ILD to about 90 ILD.

The present disclosure also provides methods for reducing the viscosity of a cell lysate or tissue lysate comprising the steps recited above, and further comprising generating the unfiltered lysate by methods comprising: separating growth media from the cells or tissue; washing the cells or tissue with wash buffer; removing the buffer from the cells or tissue; lysing the cells or tissue by adding lysis buffer, wherein the lysate comprises at least 90% of polypeptides and genomic DNA extracted from the cells or tissue, and wherein the genomic DNA is not sheared; transferring the lysate having an original lysate volume to a container, such as a 15 ml conical tube; and diluting the lysate with 1×-10× volume, 3×-10× volume, or 5×-10× volume of dilution buffer to produce a diluted lysate volume.

The present disclosure also provides kits for reducing the viscosity of a cell lysate or tissue lysate comprising: lysis buffer, syringe, and compressible and open-cell foam filter having a pore size from about 0.65 mm to about 1.22 mm. In some embodiments, the foam filter has a density from about 1.3 lbs/ft$^3$ to about 3.0 lbs/ft$^3$. In some embodiments, the foam filter has an Indentation Load Deflection (ILD), also referred to as Indentation Force Deflection (IFD), from about 60 ILD to about 90 ILD. In some embodiments, the kit further comprises a dilution buffer, wash buffer, and a post-translational modification inhibitor cocktail.

BRIEF DESCRIPTION OF THE DRAWINGS

FIGS. 7A and 7B show representative data that demonstrates the recovery of polypeptides from a Laemmli buffer lysate that has been passed over a filter as described herein.

FIG. 9 shows a table of representative polyurethane filter properties.

DESCRIPTION OF EMBODIMENTS

Figure 1:
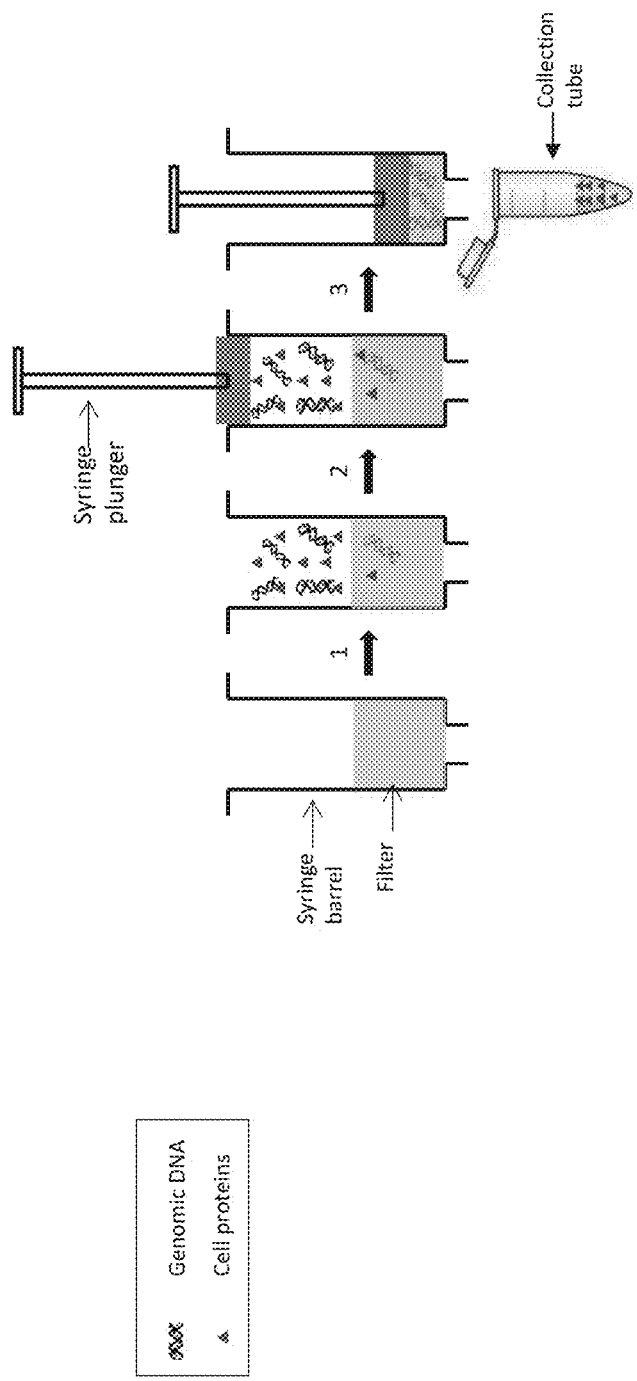
FIG. 1 shows a representative schematic of a composition and operation of the filter system.

Unless defined otherwise, all technical and scientific terms have the same meaning as is commonly understood by one of ordinary skill in the art to which the embodiments disclosed belongs.

As used herein, the terms "a" or "an" means "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments. For example, the phrase "about 10" means a range from 9 to 11.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps.

As used herein, the term "contacting" refers to the bringing together of any lysate described herein with any filter described herein.

It is further appreciated that certain features which are, for clarity, described in the context of separate embodiments, can also be provided in combination in a single embodiment. Conversely, various features which are, for brevity, described in the context of a single embodiment, can also be provided separately or in any suitable sub-combination.

The present disclosure provides methods for reducing the viscosity of a cell lysate or tissue lysate comprising: contacting the cell lysate or tissue lysate with a compressible and open-cell foam filter having a pore size from about 0.65 mm to about 1.22 mm, wherein the filter is present in a syringe; compressing the filter to recover the lysate absorbed in the filter, wherein the compression ratio is from about 50% to about 95%; and collecting the filtered lysate, wherein the filtered lysate contains at least 95% of the polypeptides in the original cell lysate or original tissue lysate, and wherein the filtered lysate contains no more than 10% of the genomic DNA in the original cell lysate or original tissue lysate.

The lysate may be derived from any cell or tissue. In some embodiments, the cell (or tissue) is an exocrine secretory epithelial cell (such as, for example, salivary gland mucous cell, salivary gland number 1 cell, Von Ebner's gland cell in tongue, mammary gland cell, lacrimal gland cell, ceruminous gland cell in ear, eccrine sweat gland dark cell, eccrine sweat gland clear cell, apocrine sweat gland cell, gland of Moll cell in eyelid, sebaceous gland cell, Bowman's gland cell in nose, Brunner's gland cell in duodenum, seminal vesicle cell, prostate gland cell, bulbourethral gland cell, Bartholin's gland cell, Gland of Littre cell, uterus endometrium cell, isolated goblet cell of respiratory and digestive tracts, stomach lining mucous cell, gastric gland zymogenic cell, gastric gland oxyntic cell, pancreatic acinar cell, Paneth cell of small intestine, Type II pneumocyte of lung, and Clara cell of lung).

In some embodiments, the cell (or tissue) is a hormone-secreting cell (such as, for example, anterior pituitary cell, intermediate pituitary cell, magnocellular neurosecretory cell, gut and respiratory tract cell, thyroid gland cell (such as, for example, thyroid epithelial cell and parafollicular cell), parathyroid gland cell (such as, for example, parathyroid chief cell and oxyphil cell), adrenal gland cell (such as, for example, chromaffin cell), Leydig cell of testes, Theca interna cell of ovarian follicle, corpus luteum cell of ovarian follicle (such as, for example, granulosa lutein cells and theca lutein cells), juxtaglomerular cell, macula densa cell of kidney, peripolar cell of kidney, and mesangial cell of kidney).

In some embodiments, the cell (or tissue) is a keratinizing epithelial cell (such as, for example, epidermal keratinocyte, epidermal basal cell, keratinocyte of fingernail and toenail, nail bed basal cell, medullary hair shaft cell, cortical hair shaft cell, cuticular hair shaft cell, cuticular hair root sheath cell, hair root sheath cell of Huxley's layer, hair root sheath cell of Henle's layer, external hair root sheath cell, and hair matrix cell).

In some embodiments, the cell (or tissue) is a wet stratified barrier epithelial cell (such as, for example, surface epithelial cell of stratified squamous epithelium of cornea, tongue, oral cavity, esophagus, anal canal, distal urethra and vagina, basal cell of epithelia of cornea, tongue, oral cavity, esophagus, anal canal, distal urethra and vagina, and urinary epithelium cell).

In some embodiments, the cell (or tissue) is a cell of the nervous system (such as, for example, a sensory transducer cell (such as, for example, auditory inner hair cell of organ of Corti, auditory outer hair cell of organ of Corti, basal cell of olfactory epithelium, cold-sensitive primary sensory neuron, heat-sensitive primary sensory neuron, Merkel cell of epidermis, olfactory receptor neuron, pain-sensitive primary sensory neuron, photoreceptor cell of retina in eye (such as for example, photoreceptor rod cells, photoreceptor blue-sensitive cone cell of eye, photoreceptor green-sensitive cone cell of eye, and photoreceptor red-sensitive cone cell of eye), proprioceptive primary sensory neuron, touch-sensitive primary sensory neuron, Type I carotid body cell, Type II carotid body cell, Type I hair cell of vestibular system of ear, Type II hair cell of vestibular system of ear, and Type I taste bud cell), an autonomic neuron cell (such as, for example, cholinergic neural cell, adrenergic neural cell, and peptidergic neural cell), a sense organ and peripheral neuron supporting cell (such as, for example, inner pillar cell of organ of Corti, outer pillar cell of organ of Corti, inner phalangeal cell of organ of Corti, outer phalangeal cell of organ of Corti, border cell of organ of Corti, Hensen cell of organ of Corti, vestibular apparatus supporting cell, taste bud supporting cell, olfactory epithelium supporting cell, Schwann cell, satellite glial cell, and enteric glial cell), a central nervous system neuron (such as, for example, glial cell, astrocyte, oligodendrocyte, and spindle neuron), and lens cell (such as, for example, anterior lens epithelial cell and crystallin-containing lens fiber cell)).

In some embodiments, the cell (or tissue) is a metabolism and storage cell (such as, for example, a hepatocyte, adipocyte (such as, for example, white fat cell and brown fat cell), and liver lipocyte.

In some embodiments, the cell (or tissue) is a barrier function cell (such as, for example, a kidney parietal cell, kidney glomerulus podocyte, kidney proximal tubule brush border cell, Loop of Henle thin segment cell, kidney distal tubule cell, kidney collecting duct cell, Type I pneumocyte, pancreatic duct cell, nonstriated duct cell, duct cell, intestinal brush border cell, exocrine gland striated duct cell, gall bladder epithelial cell, ductulus efferens nonciliated cell, epididymal principal cell, and epididymal basal cell).

In some embodiments, the cell (or tissue) is an extracellular matrix cell (such as, for example, ameloblast epithelial cell, planum semilunatum epithelial cell of vestibular system of ear, Organ of Corti interdental epithelial cell, loose connective tissue fibroblast, corneal fibroblast, tendon fibroblast, bone marrow reticular tissue fibroblast, other nonepithelial fibroblast, pericyte, nucleus pulposus cell of intervertebral disc, cementoblast/cementocyte, odontoblast/odontocyte, hyaline cartilage chondrocyte, fibrocartilage chondrocyte, elastic cartilage chondrocyte, osteoblast/osteocyte, osteoprogenitor cell, hyalocyte of vitreous body of eye, stellate cell of perilymphatic space of ear, hepatic stellate cell, and pancreatic stelle cell).

In some embodiments, the cell (or tissue) is a contractile cell (such as, for example, skeletal muscle cell (such as, for example, red skeletal muscle cell, white skeletal muscle cell, intermediate skeletal muscle cell, nuclear bag cell of muscle spindle, and nuclear chain cell of muscle spindle), satellite cell, heart muscle cell (such as, for example, nodal heart muscle cell and Purkinje fiber cell), smooth muscle cell, myoepithelial cell of iris, and myoepithelial cell of exocrine glands).

In some embodiments, the cell (or tissue) is a blood and/or immune system cell (such as, for example, monocyte, macrophage, epidermal Langerhans cell, osteoclast, dendritic cell, microglial cell, neutrophil granulocyte, eosinophil granulocyte, basophil granulocyte, mast cell, T cell (such as, for example, helper T cell, suppressor T cell, cytotoxic T cell, and natural killer T cell), B cell, natural killer cell, and reticulocyte).

In some embodiments, the cell (or tissue) is a germ cell (such as, for example, oogonium/oocyte, spermatid, spermatocyte, spermatogonium cell, and spermatozoon) or a nurse cell (such as, for example, ovarian follicle cell), Sertoli cell, and thymus epithelial cell).

In some embodiments, the cell (or tissue) is a stem cell, stem cell progenitor cell, cell line, or hybridoma of any of the cells described herein.

In some embodiments, the cell (or tissue) is eukaryotic. Eukaryotic cells include animal cells and plant cells. Animal cells include cells (or tissue) from, for example, humans and non-human vertebrates such as wild, domestic and farm animals. In some embodiments, the animal cell is a mammals, such as mice, rats, other rodents, rabbits, dogs, cats, swine, cattle, sheep, horses, or primates. In some embodiments, the cell (or tissue) is prokaryotic, including, for example, bacteria, fungi, and protozoans.

In some embodiments, the viscosity is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the viscosity is reduced by at least 90%.

In some embodiments, the compressible and open-cell foam filter has pores ranging in size from about 0.10 mm to about 2.50 mm, from about 0.25 mm to about 2.00 mm, from about 0.50 mm to about 1.50 mm, from about 0.60 mm to about 1.4 mm, or from about 0.65 mm to about 1.22 mm. In some embodiments, the compressible and open-cell foam filter has a pore size of about 0.7 mm.

In some embodiments, the density of the filter ranges from about 1.3 to about 3.0 lb/ft$^3$, from about 1.3 to about 2.0 lb/ft$^3$, from about 1.2 to about 1.6 lb/ft$^3$, or from about 1.4 to about 1.5 lb/ft$^3$. In some embodiments, the density of the filter is about 1.4 lb/ft$^3$.

In some embodiments, the Indentation Force Deflection (IFD) ranges from about 60 to about 90 IFD, or from about 70 to about 80 IFD. In some embodiments, the Indentation Force Deflection (IFD) is 70 (IFD).

In some embodiments, the compressible and open-cell foam filter is a polyurethane foam filter. In some embodiments, the polyurethane is a polyester or polyether. The materials used to construct the foam filter can be obtained from commercial suppliers including, for example, American Foam Products (Painesville Ohio) and Wisconsin Foam Products (Madison Wis.).

In some embodiments, the compressible and open-cell foam filter is present in container. In some embodiments, the container is a syringe. In some embodiments, the filter is present in the syringe and occupies the internal space, or a portion of the internal space, of the syringe. In some embodiments, the volume of the syringe is 1 ml, 3 ml, 5 ml, 10 ml, 20 ml, 25 ml, 30 ml, 50 ml, 60 ml, 100 ml, or 200 ml. Any type of compression device that allows even weight distribution to be exerted on the filter can be used. For example, a cylinder provides a suitable shape and manual operation of the syringe plunger, which provides a simple and effective method of exerting the compression. However, one skilled in the art can use automated devices of different shapes.

In some embodiments, the cell lysate or tissue lysate is contacted with the compressible and open-cell foam filter by layering or pouring the cell lysate or tissue lysate on top of the filter within the syringe. The cell lysate or tissue lysate is absorbed by the filter. Not desiring to be bound by theory, the cellular polypeptides will pass through the filter and form a portion of the filtered lysate, whereas the genomic DNA will be retained by the filter.

The filter is compressed to recover the lysate absorbed in the filter. The recovered lysate is referred to herein as filtered lysate. In some embodiments, the compression ratio is from about 30% to about 99%, from about 35% to about 98%, from about 40% to about 98%, from about 45% to about 98%, or from about 50% to about 95%. When the filter is within a syringe for example, the plunger can be activated to compress the filter. In some embodiments, the filter may be washed in re-used.

The filtered lysate is collected and contains at least 75%, at least 80%, at least 85%, at least 90%, or at least 95% of the polypeptides in the original cell lysate or original tissue lysate. In contrast, the filtered lysate contains no more than 30%, no more than 25%, no more than 20%, no more than 15%, or no more than 10% of the genomic DNA in the original cell lysate or original tissue lysate.

In some embodiments, the ratio of the volume of the lysate to filter is from 0.1:1 to 4:1, from 0.1:1 to 2:1, or from 1:1 to 2:1. Thus, for example, if the filter volume is 10 ml, the lysate volume can be 1 ml to 40 ml (i.e., from 0.1:1 to 4:1), 1 ml to 20 ml (i.e., from 0.1:1 to 2:1), 10 ml to 20 ml (i.e., from 1:1 to 2:1).

In some embodiments, the volume of the lysate is from 0.01 ml to 10,000 ml, from 0.1 ml to 1,000 ml, from 0.5 ml to 500 ml, from 1 ml to 200 ml, or from 1 ml to 100 ml.

In some embodiments, the methods for reducing the viscosity of a cell lysate or tissue lysate as described herein further comprise determining the amount of protein in the filtered lysate. The amount can be determined by any standard technique known to one skilled in the art. For example, the absorbance of the lysate sample can be measured at 600 nm (i.e., $OD_{600}$). The lysate protein concentration can be calculated therefrom. In some embodiments, the lysate is diluted prior to determining the protein concentration.

In some embodiments, the methods for reducing the viscosity of a cell lysate or tissue lysate as described herein further comprise diluting the filtered lysate with 1×-10× volume, 3×-10× volume, or 5×-10× volume of dilution buffer to produce a diluted filtered lysate. In some embodiments, the dilution buffer comprises a detergent, a salt, and a protease inhibitor. In some embodiments, the detergent is Triton™ X-100, Tween® 20, or IGEPAL® (octylphenoxy poly(ethyleneoxy)ethanol, branched), or the like. In some embodiments, the salt is sodium chloride or potassium chloride, or the like. In some embodiments, the protease inhibitor is chymotrypsin, pepstatin, aprotinin, phenylmethylsulfonyl fluoride (PMSF), bestatin, leupeptin, or ethylenediaminetetraacetic acid (EDTA), or the like.

In some embodiments, the methods for reducing the viscosity of the cell lysate or tissue lysate as described herein further comprise generating the original unfiltered lysate (prior to contacting the cell lysate or tissue lysate with the compressible and open-cell foam filter) by methods comprising: separating growth media from the cells or tissue; washing the cells or tissue with wash buffer; removing the buffer from the cells or tissue; lysing the cells or tissue by adding lysis buffer, wherein the lysate comprises at least 90% of polypeptides and genomic DNA extracted from the cells or tissue, and wherein the genomic DNA is not sheared; transferring the lysate having an original lysate volume to a container; and diluting the lysate with dilution buffer to produce a diluted lysate volume.

In some embodiments, the cells or tissue are in culture with growth medium. The growth media can be separated from the cells or tissue by aspirating the growth media from the culture dish or flask containing the cells or tissue, such as when the cells or tissue are adherent to the culture dish or flask. Alternately, the adherent cells or tissue in the culture dish or flask can be scraped by conventional techniques such that they become suspended in the growth media. For scraped adherent cells or for non-adherent cells, the growth media can be separated from the cells or tissue by conventional centrifugation resulting in a cell pellet.

In some embodiments, the cells or tissue are washed with wash buffer. In some embodiments, the wash buffer comprises a physiological buffer such as, for example, phosphate buffered saline (PBS), or the like. Additional buffers include, but are not limited to, tris-buffered saline (TBS), Dulbecco's phosphate buffered saline (DPBS), and 50 mM piperazine-N,N'-bis(2-ethanesulfonic acid) (PIPES). In some embodiments, the wash buffer contains post-translational modification (PTM) inhibitors including, but not limited to, orthovanadate, N-ethylmaleimide, and Trichostatin A.

In some embodiments, the wash buffer is removed from the cells or tissue. For example, the wash buffer can be removed by conventional centrifugation resulting in a cell pellet, and aspirating the wash growth media from the cell pellet.

In some embodiments, the cells (or cells from the tissue) are lysed by adding lysis buffer. In some embodiments, the lysis buffer comprises a post-translational modification inhibitor cocktail. In some embodiments, the post-translational modification inhibitor cocktail comprises one or more of a de-ubiquitin inhibitor, a phosphotyrosine inhibitor, a de-SUMOylation inhibitor, a phosphoserine inhibitor, a phosphothreonine inhibitor, a de-acetylase inhibitor, and a de-methylase inhibitor. Phosphotyrosine inhibitors include, but are not limited to, orthovanadate, molybdate, and phenylaraine oxide. De-SUMOylation inhibitors include, but are not limited to, N-ethylmaleimide. De-ubiquitination inhibitors include, but are not limited to, N-ethylmaleimide and WP1130. De-acetylation inhibitors include, but are not limited to, Trichostatin A, EX-527, and nicotinamide. De-methylase inhibitors include, but are not limited to, tranylcypromine hydrochloride.

In some embodiments, the lysis buffer comprises a detergent and a reducing agent. Suitable detergents include, but are not limited to, 3-[(3-Cholamidopropyl) dimethylammonio]-1-propanesulfonate (CHAPS), Tween® 20, Triton™ X-100, Tween® 80, Brij-35, sodium deoxycholate, IGEPAL, nonyl phenoxypolyethoxylethanol (NP40), and sodium dodecyl sulphate (SDS). In some embodiments, the reducing agent is 2-mercaptoethanol. In some embodiments, the lysis buffer comprises a detergent, a chaotrope, and a protease inhibitor. Suitable chaotropes include, but are not limited to, guanidinium chloride, lithium perchlorate, lithium acetate, SDS, thiourea, and urea. In some embodiments, upon lysis of the cells, the lysate comprises at least 70%, at least 75%, at least 80%, at least 85%, or at least 90% of the polypeptides and genomic DNA originally present in the cells (or cells from the tissue). In some embodiments, the genomic DNA is not sheared or is not significantly sheared. In embodiments where the genomic DNA is not significantly sheared, less than 20%, less than 15%, less than 10%, less than 5%, or less than 1% of the original amount of genomic DNA is sheared. The resultant lysate has an original lysate volume.

In some embodiments, the original lysate volume of the lysate is transferred to a container, such as a 15 ml conical tube, a microfuge tube, or a 2 ml tube.

In some embodiments, the lysate is further diluted with dilution buffer to produce a diluted lysate volume. In some embodiments, the lysate is diluted with 1×-10× volume, 3×-10× volume, or 5×-10× volume of dilution buffer. In some embodiments, the dilution buffer comprises a detergent, a salt, and a protease inhibitor, such as those described herein. In some embodiments, the dilution buffer comprises a post-translational modification inhibitor cocktail, such as those described herein.

The methods described herein result in cell or tissue lysates that can be used in many biological or chemical assays such as, for example, Western blots, immunoprecipitation assays, quantification assays, enzyme-linked immunosorbant assays (ELISAs), protein purification methods, and the like.

The present disclosure also provides kits for reducing the viscosity of a cell lysate or tissue lysate. In some embodiments, the kits comprise: a lysis buffer, such as any of those described herein; and a syringe, such as any of those described herein; and a compressible and open-cell foam filter, such as any of those described herein. In some embodiments, the foam filter has a density as described herein. In some embodiments, the foam filter has an ILD as described herein. In some embodiments, the kit further comprises a dilution buffer, wash buffer, and a post-translational modification inhibitor cocktail, such as any of those described herein.

PD-L1 (also named B7 homolog 1 or CD274) is critical for the maintenance of T cell homeostasis and holds great promise as a target for therapeutic intervention in cancer, autoimmune diseases and infections (Ostrand-Rosenberg et al., J. Immunol., 2014, 193, 3835-3841). It is known that epidermal growth factor receptor (EGFR) pathway stimulation upregulates PD-L1 (Akbay et al., Cancer Discov., 2013, 3, 1355-1363; and Chen et al., J. Thorac. Oncol., 2015, 10, 910-923). Proteomic studies of EGF stimulated cells that express PD-L1 have failed to identify EGF stimulated PD-L1 ubiquitination (Argenzio et al., Mol. Syst. Biol., 2011, 7, 462).

The present disclosure also provides methods for detecting ubiquitinated programmed death ligand 1 (PD-L1) comprising: contacting a cell lysate or tissue lysate containing or suspected of containing ubiquitinated PD-L1 with a compressible and open-cell foam filter having a pore size from about 0.65 mm to about 1.22 mm, a density from about 1.3 lbs/ft3 to about 3.0 lbs/ft3, and an indentation load deflection (ILD) from about 60 ILD to about 90 ILD, wherein the filter is present in a syringe; compressing the filter to recover the lysate absorbed in the filter, wherein the compression ratio is from about 50% to about 95%; collecting the filtered lysate, wherein the filtered lysate contains at least 95% of the polypeptides in the original cell lysate or original tissue lysate, and wherein the filtered lysate contains no more than 10% of the genomic DNA in the original cell lysate or original tissue lysate; and detecting the presence or absence of ubiquitinated PD-L1 by contacting the filtered lysate with an anti-ubiquitin agent and an anti-PD-L1 agent. In some embodiments, the anti-ubiquitin agent is an anti-ubiquitin antibody or ubiquitin affinity beads. In some embodiments, the anti-PD-L1 agent is an anti-PD-L1 antibody. In some embodiments, the filtered lysate is contacted first with the anti-ubiquitin agent to immunoprecipitate ubiquitinated proteins, and then the ubiquitinated proteins are contacted by the anti-PD-L1 agent to detect ubiquitinated PD-L1. In some embodiments, the filtered lysate is contacted first with the anti-PD-L1 agent to immunoprecipitate PD-L1 proteins, and then the PD-L1 proteins are contacted by the anti-ubiquitin agent to detect ubiquitinated PD-L1. In some embodiments, a secondary antibody-detection system is used to detect the anti-PD-L1 agent. In some embodiments, the secondary antibody-detection system is a colorimetric, enzymatic, chemiluminescent, radioisotopic, colloidal gold, or fluorescence reporter system. In some embodiments, the secondary antibody-detection system is a secondary antibody conjugated to an enzyme. In some embodiments, the enzyme is alkaline phosphatase (AP) or horseradish peroxidase (HRP).

The present disclosure provides methods for detecting ubiquitinated PD-L1, as described herein, using the any of the embodiments of the compressible and open-cell foam filter, as described herein, by any of the methods for reducing the viscosity of a cell lysate or tissue lysate described herein.

The present disclosure provides the following representative embodiments:

Embodiment 1

A method for reducing the viscosity of a cell lysate or tissue lysate comprising: contacting the cell lysate or tissue lysate with a compressible and open-cell foam filter having a pore size from about 0.65 mm to about 1.22 mm, a density from about 1.3 lbs/ft$^3$ to about 3.0 lbs/ft$^3$, and an indentation load deflection (ILD) from about 60 ILD to about 90 ILD, wherein the filter is present in a syringe; compressing the filter to recover the lysate absorbed in the filter, wherein the compression ratio is from about 50% to about 95%; and collecting the filtered lysate, wherein the filtered lysate contains at least 95% of the polypeptides in the original cell lysate or original tissue lysate, and wherein the filtered lysate contains no more than 10% of the genomic DNA in the original cell lysate or original tissue lysate.

Embodiment 2

The method of embodiment 1, wherein the compressible and open-cell foam filter is a polyurethane foam.

Embodiment 3

The method of embodiment 2, wherein the polyurethane is a polyester or polyether.

Embodiment 4

The method of any one of embodiments 1 to 3, wherein the ratio of the volume of the lysate to filter is from 0.1 to 4, from 0.1 to 2, or from 1 to 2.

Embodiment 5

The method of any one of embodiments 1 to 4, wherein the volume of the lysate is from 0.1 ml to 1,000 ml, from 0.5 ml to 500 ml, from 1 ml to 200 ml, or from 1 ml to 100 ml.

Embodiment 6

The method of any one of embodiments 1 to 5, further comprising determining the amount of protein in the filtered lysate.

Embodiment 7

The method of any one of embodiments 1 to 6, wherein the cells or tissue are eukaryotic.

Embodiment 8

The method of any one of embodiments 1 to 6, wherein the cells or tissue are prokaryotic.

Embodiment 9

The method of any one of embodiments 1 to 8, further comprising diluting the filtered lysate with 1×-10× volume, 3×-10× volume, or 5×-10× volume of dilution buffer to produce a diluted filtered lysate.

Embodiment 10

The method of embodiment 10, wherein the dilution buffer comprises a detergent, a salt, and a protease inhibitor.

Embodiment 11

The method of any one of embodiments 1 to 10, wherein the unfiltered lysate is generated by a method comprising: separating growth media from the cells or tissue; washing the cells or tissue with wash buffer; removing the buffer from the cells or tissue; lysing the cells or tissue by adding lysis buffer, wherein the lysate comprises at least 90% of polypeptides and genomic DNA extracted from the cells or tissue, and wherein the genomic DNA is not sheared; transferring the lysate having an original lysate volume to a container, such as a 15 ml conical tube; and diluting the lysate with dilution buffer to produce a diluted lysate volume.

Embodiment 12

The method of embodiment 11, wherein either or both of the lysis buffer and dilution buffer comprise a post-translational modification inhibitor cocktail.

Embodiment 13

The method of embodiment 11 or embodiment 12, wherein the post-translational modification inhibitor cocktail comprises one or more of a de-ubiquitin inhibitor, a phosphotyrosine inhibitor, a de-SUMOylation inhibitor, a phosphoserine inhibitor, a phosphothreonine inhibitor, a de-acetylase inhibitor, and de-methylase inhibitor.

Embodiment 14

The method of any one of embodiments 11 to 13, wherein the lysis buffer comprises a detergent and a reducing agent.

Embodiment 15

The method of any one of embodiments 11 to 14, wherein the lysis buffer comprises a detergent, a chaotrope, and a protease inhibitor.

Embodiment 16

The method of any one of embodiments 11 to 15, wherein the wash buffer comprises a physiological buffer.

Embodiment 17

The method of any one of embodiments 11 to 16, wherein the dilution buffer comprises a detergent, a salt, and a protease inhibitor.

Embodiment 18

The method of any one of embodiments 11 to 17, wherein the lysate is diluted with 1×-10× volume, 3×-10× volume, or 5×-10× volume of dilution buffer to produce the diluted lysate volume.

Embodiment 19

The method of any one of embodiments 1 to 18, further comprising determining the lysate protein concentration using a colorimetric protein concentration assay.

Embodiment 20

The method of any one of embodiments 1 to 18, further comprising detecting multiple protein post-translational modifications in the lysate.

Embodiment 21

A kit for reducing the viscosity of a cell lysate or tissue lysate comprising: lysis buffer; syringe; and compressible and open-cell foam filter having a pore size from about 0.65 mm to about 1.22 mm.

Embodiment 22

The kit of embodiment 21, further comprising a dilution buffer, a wash buffer, and a post-translational modification inhibitor cocktail.

Embodiment 23

The kit of embodiment 21 or embodiment 22, wherein the filter is present in the syringe and occupies the internal space of the syringe.

Embodiment 24

The kit of any one of embodiments 21 to 23, wherein the compressible and open-cell foam filter is a polyurethane foam.

Embodiment 25

The kit of any one of embodiments 21 to 24, wherein the polyurethane is a polyester or polyether.

Embodiment 26

The kit of any one of embodiments 21 to 25, wherein the dilution buffer comprises a detergent, a salt, and a protease inhibitor.

Embodiment 27

The kit of any one of embodiments 21 to 26, wherein either or both of the lysis buffer and dilution buffer comprise a post-translational modification inhibitor cocktail.

Embodiment 28

The kit of embodiment 27, wherein the post-translational modification inhibitor cocktail comprises one or more of a de-ubiquitin inhibitor, a phosphotyrosine inhibitor, a de- SUMOylation inhibitor, a phosphoserine inhibitor, a phosphothreonine inhibitor, a de-acetylase inhibitor, and de-methylase inhibitor.

Embodiment 29

The kit of any one of embodiments 21 to 28, wherein the lysis buffer comprises a detergent and a reducing agent.

Embodiment 30

The kit of any one of embodiments 21 to 29, wherein the lysis buffer comprises a detergent, a chaotrope, and a protease inhibitor.

Embodiment 31

The kit of any one of embodiments 21 to 30, wherein the wash buffer comprises a physiological buffer.

Embodiment 32

The kit of any one of embodiments 21 to 30, wherein the de-ubiquitin inhibitor is N-ethylmaleimide.

Embodiment 33

A method for detecting ubiquitinated programmed death ligand 1 (PD-L1) comprising: contacting a cell lysate or tissue lysate containing or suspected of containing ubiquitinated PD-L1 with a compressible and open-cell foam filter having a pore size from about 0.65 mm to about 1.22 mm, a density from about 1.3 lbs/ft3 to about 3.0 lbs/ft3, and an indentation load deflection (ILD) from about 60 ILD to about 90 ILD, wherein the filter is present in a syringe; compressing the filter to recover the lysate absorbed in the filter, wherein the compression ratio is from about 50% to about 95%; collecting the filtered lysate, wherein the filtered lysate contains at least 95% of the polypeptides in the original cell lysate or original tissue lysate, and wherein the filtered lysate contains no more than 10% of the genomic DNA in the original cell lysate or original tissue lysate; and detecting the presence or absence of ubiquitinated PD-L1 by contacting the filtered lysate with an anti-ubiquitin agent and an anti-PD-L1 agent.

Embodiment 34

The method of embodiment 33, wherein the anti-ubiquitin agent is an anti-ubiquitin antibody or ubiquitin affinity beads.

Embodiment 35

The method of embodiment 33 or embodiment 34, wherein the anti-PD-L1 agent is an anti-PD-L1 antibody.

Embodiment 36

The method of any one of embodiments 33 to 35, wherein the filtered lysate is contacted first with the anti-ubiquitin agent to immunoprecipitate ubiquitinated proteins, and then the ubiquitinated proteins are contacted by the anti-PD-L1 agent to detect ubiquitinated PD-L1.

Embodiment 37

The method of any one of embodiments 33 to 36, wherein a secondary antibody-detection system is used to detect the anti-PD-L1 agent.

Embodiment 38

The method of embodiment 37, wherein the secondary antibody-detection system is a colorimetric, enzymatic, chemiluminescent, radioisotopic, colloidal gold, or fluorescence reporter system.

Embodiment 39

The method of embodiment 37, wherein the secondary antibody-detection system is a secondary antibody conjugated to an enzyme.

Embodiment 40

The method of embodiment 39, wherein the enzyme is alkaline phosphatase (AP) or horseradish peroxidase (HRP).

Embodiment 41

The method of any one of embodiments 33 to 39, wherein the compressible and open-cell foam filter is a polyurethane foam.

Embodiment 42

The method of embodiment 41, wherein the polyurethane is a polyester or polyether.

Embodiment 43

The method of any one of embodiments 33 to 42, wherein the ratio of the volume of the lysate to filter is from 0.1 to 4, from 0.1 to 2, or from 1 to 2.

Embodiment 44

The method of any one of embodiments 33 to 43, wherein the volume of the lysate is from 0.1 ml to 1,000 ml, from 0.5 ml to 500 ml, from 1 ml to 200 ml, or from 1 ml to 100 ml.

Embodiment 45

The method of any one of embodiments 33 to 44, further comprising determining the amount of protein in the filtered lysate.

Embodiment 46

The method of any one of embodiments 33 to 45, further comprising diluting the filtered lysate with 1×-10× volume, 3×-10× volume, or 5×-10× volume of dilution buffer to produce a diluted filtered lysate.

Embodiment 47

The method of embodiment 46, wherein the dilution buffer comprises a detergent, a salt, and a protease inhibitor.

Embodiment 48

The method of any one of embodiments 33 to 47, wherein the unfiltered lysate is generated by a method comprising: separating growth media from the cells or tissue; washing the cells or tissue with wash buffer; removing the buffer from the cells or tissue; lysing the cells or tissue by adding lysis buffer, wherein the lysate comprises at least 90% of polypeptides and genomic DNA extracted from the cells or tissue, and wherein the genomic DNA is not sheared; transferring the lysate having an original lysate volume to a container, such as a 15 ml conical tube; and diluting the lysate with dilution buffer to produce a diluted lysate volume.

Embodiment 49

The method of embodiment 48, wherein either or both of the lysis buffer and dilution buffer comprise a post-translational modification inhibitor cocktail.

Embodiment 50

The method of embodiment 48 or embodiment 49, wherein the post-translational modification inhibitor cocktail comprises one or more of a de-ubiquitin inhibitor, a phosphotyrosine inhibitor, a de-SUMOylation inhibitor, a phosphoserine inhibitor, a phosphothreonine inhibitor, a de-acetylase inhibitor, and de-methylase inhibitor.

Embodiment 51

The method of any one of embodiments 48 to 50, wherein the lysis buffer comprises a detergent and a reducing agent.

Embodiment 52

The method of any one of embodiments 48 to 51, wherein the lysis buffer comprises a detergent, a chaotrope, and a protease inhibitor.

Embodiment 53

The method of any one of embodiments 48 to 53, wherein the wash buffer comprises a physiological buffer.

Embodiment 54

The method of any one of embodiments 48 to 53, wherein the dilution buffer comprises a detergent, a salt, and a protease inhibitor.

Embodiment 55

The method of any one of embodiments 48 to 54, wherein the lysate is diluted with 1×-10× volume, 3×-10× volume, or 5×-10× volume of dilution buffer to produce the diluted lysate volume.

Embodiment 56

The method of any one of embodiments 33 to 55, further comprising determining the lysate protein concentration using a colorimetric protein concentration assay.

Embodiment 57

The method of any one of embodiments 33 to 56, further comprising detecting multiple protein post-translational modifications in the lysate.

In order that the subject matter disclosed herein may be more efficiently understood, examples are provided below. It should be understood that these examples are for illustrative purposes only and are not to be construed as limiting the claimed subject matter in any manner Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Composition and Use of Filter System

Referring to FIG. 1, a cell or tissue lysate that includes un-sheared genomic DNA and proteins was placed on a filter that is housed in a syringe structure. The filter was compressed to about 5% of its original volume, resulting in cellular proteins being released into a collection vessel while genomic DNA remains trapped in the filter. FIG. 1 demonstrates a mechanism of action of the filter system and the requirement for compression of the filter to recover cellular protein from the original lysate. It also demonstrates the stand alone nature of operation of the filter in that no other equipment, such as a centrifuge or vacuum system is necessary for operation. Three steps are shown in FIG. 1. First, a cell lysate containing genomic DNA and proteins was placed on the filter. Second, a compression device (such as a syringe plunger in FIG. 1) was inserted into the syringe barrel. Third, the filter was compressed to 5-50% of the original filter volume causing cellular proteins to be eluted into a collection tube. Genomic DNA was trapped and remained in the filter. The trapping of genomic DNA causes a reduction of viscosity in the eluted protein fraction.

Example 2: Removal of Genomic DNA from A431 Cell Lysate after Filtering

Figure 2:
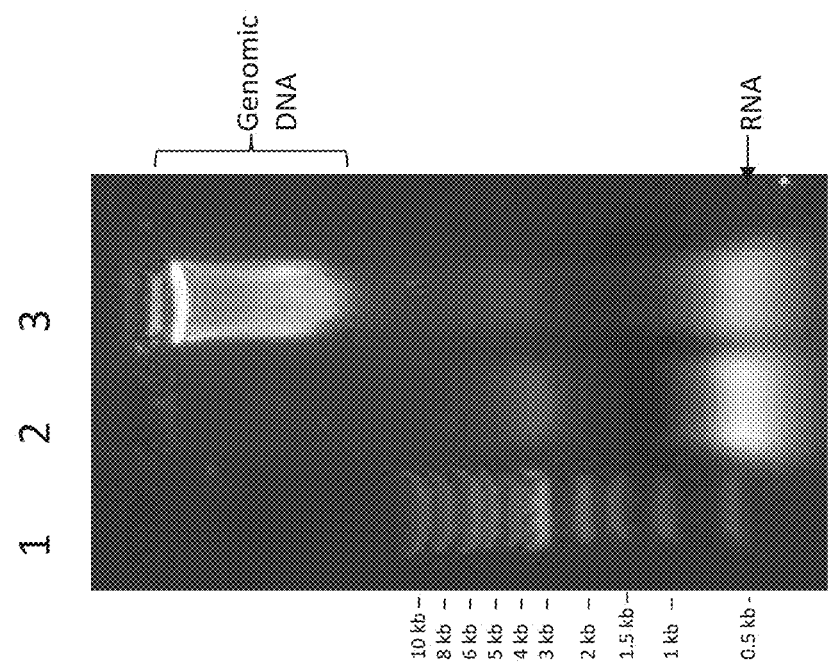
FIG. 2 shows a representative gel showing genomic DNA recovered from lysates of 80% confluent mammalian A431 epidermoid carcinoma cells which have been filtered or not filtered by the methods described herein.

Referring to FIG. 2, a representative gel shows genomic DNA recovered from lysates of 80% confluent mammalian A431 epidermoid carcinoma cells which have been filtered or have not been filtered by the methods described herein. The cell line A431 was used in this example. Approximately $1.6 \times 10^7$ cells were lysed in a denaturing lysis buffer under conditions in which genomic DNA remained unsheared. A sample of the viscous lysate that contained cellular proteins of interest was passed over the filter (see, Lane 2). An equal volume of the viscous lysate was not passed over the filter and the genomic DNA was sheared by multiple rounds of passage through a narrow gauge needle (see, Lane 3). Both lysates were run on an agarose gel and nucleic acids were visualized by staining with ethidium bromide. Genomic DNA was visualized in FIG. 2 (see, Lane 3) as a brightly stained species running at a molecular weight above 10 kb. RNA was visualized as brightly stained species running at around 500 bp (see, Lanes 2 & 3). The data from this figure demonstrates that the filter system can remove the majority of genomic DNA from the mammalian cell lysate.

In particular, $16 \times 10^6$ of A431 cells were lysed with 600 µl of denaturing lysis buffer. The lysate was filter as described herein. 2% of the lysate was analyzed by ethidium bromide agarose gel electrophoresis. Lane 1 shows a DNA ladder, Lane 2 shows the lysate after filtering, and Lane 3 shows the lysate before filtering.

Example 3: Removal of Genomic DNA from E. coli Cell Lysate after Filtering

Figure 3:
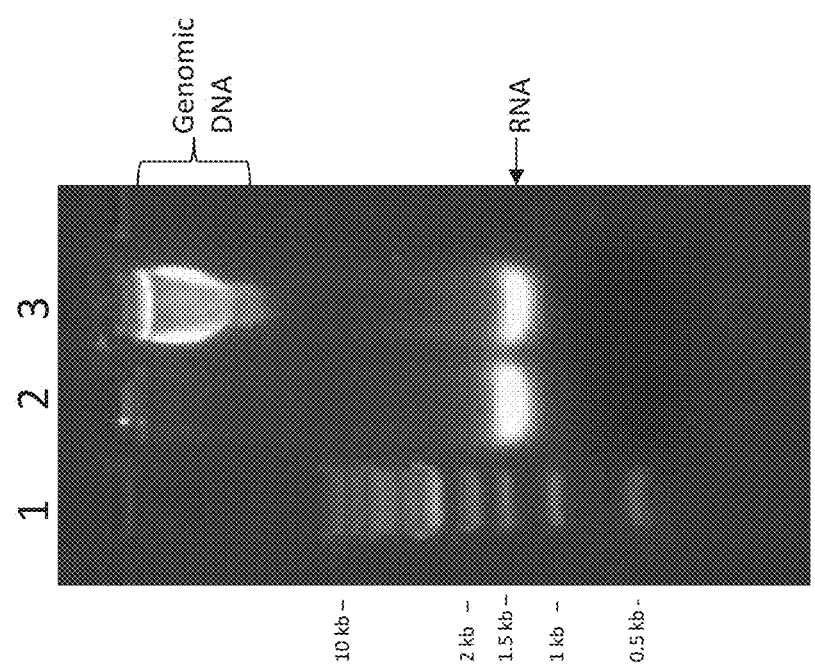
FIG. 3 shows a representative gel showing genomic DNA recovered from lysates of *E. coli* cells which have been filtered or not filtered by methods described herein.

Referring to FIG. 3, a representative gel shows genomic DNA recovered from lysates of *E. coli* cells which have been filtered or not filtered by methods described herein. *E. coli* cells were grown in LB media. $9 \times 10^9$ cells were pelleted and lysed with 1 ml of lysis buffer. The lysate was filtered as described herein. 2% of the lysate was analyzed by ethidium bromide agarose gel electrophoresis. Genomic DNA was visualized in FIG. 3 (see, Lane 3) as a brightly stained species running at a molecular weight above 10 kb. RNA was visualized as brightly stained species running at around 1.5 kb (see, Lanes 2 & 3). The data from this figure demonstrates that the filter system can remove the majority of genomic DNA from the bacterial cell lysate. For the better visualization before loading, lysates were passed through a 30 gauge needle three times. Lane 1 shows a DNA ladder, Lane 2 shows the lysate after filtering, and Lane 3. shows the lysate before filtering.

Example 4: Lysate Viscosity Reduction after Filtering

Figure 4:
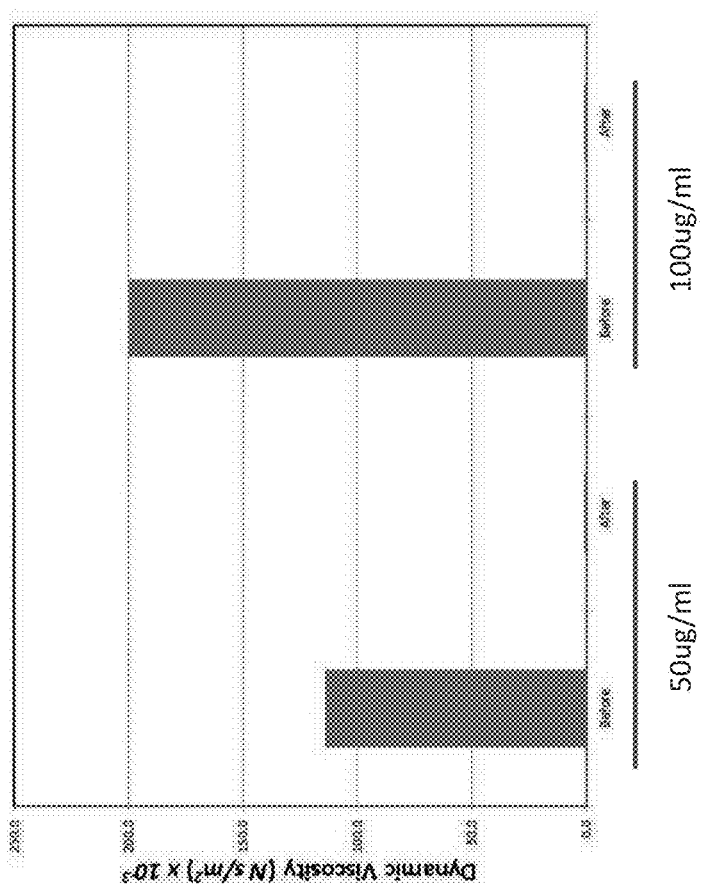
FIG. 4 shows representative data for measuring the reduction in viscosity achieved by passing a cell lysate over a filter as described herein.

Referring to FIG. 4, representative data for measuring the reduction in viscosity achieved by passing a cell lysate over the filter is shown. A431 cells were grown to confluency, achieving final genomic DNA concentrations of 50 µg/ml ($8 \times 10^6$ cells) and 100 µg/ml ($1.6 \times 10^7$ cells), respectively, when cells were lysed in 600 µl of denaturing lysis buffer. Dynamic viscosities were measured by the Falling Sphere Viscometer method (Cho Y. T. & Hartnett J. P. 1979. The falling ball viscometer—a new instrument for viscoelastic fluids. Lett. In heat and mass transfer. 6: 335-342) at room temperature and recorded values were expressed in Newton-seconds per square meter. Glycerol solutions of 60%, 70%, 80%, 90% and 95% were used as calibration standards to generate a standard curve for the lysate viscosity calculations. The data presented in FIG. 4 demonstrates that the filter can dramatically reduce the viscosity of a cell or tissue lysate that contained un-sheared genomic DNA. Lysate viscosity can dramatically interfere with downstream processes of protein analysis such as immunoprecipitations, protein purifications, or western blot analysis.

Example 5: Polypeptide Recovery of Lysates after Filtering

Figure 5C:
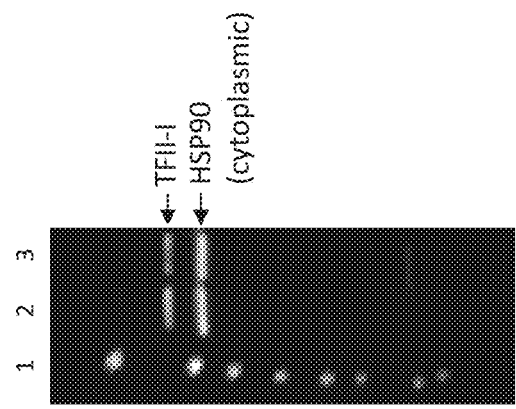
FIGS. 5A, 5B, and 5C show representative data that demonstrates the recovery of polypeptides from a denaturing buffer lysate that has been passed over a filter as described herein.
Figure 5B:
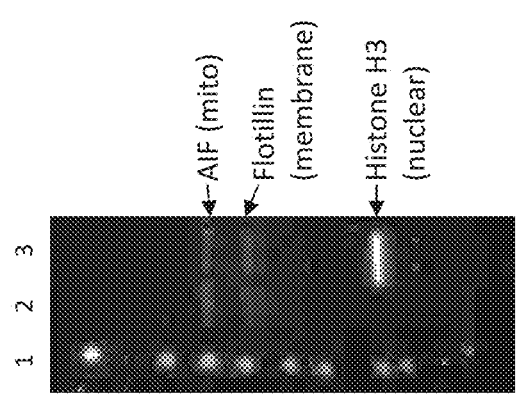
Figure 5A:
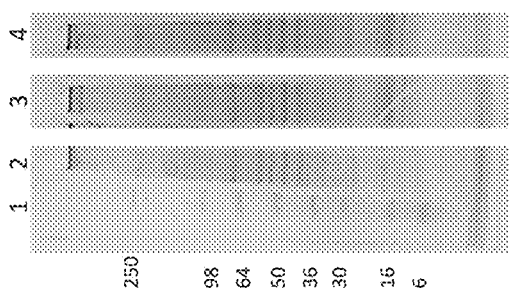

Referring to FIGS. 5A, 5B, and 5C, representative data that demonstrates the recovery of polypeptides from a denaturing buffer lysate that has been passed over a filter is shown. Referring to FIG. 5A, A431 cells were lysed with either RIPA buffer (see, Lane 2) or denaturing buffer (see, Lanes 3 and 4). The lysates were untreated (see, Lane 2), passed over the filter (see, Lane 3), or treated with the DNA digesting enzyme Benzonase® (see, Lane 4). Samples were then mixed with an equal volume of 2× Laemmli buffer and run on SDS-PAGE. Polypeptides were visualized by staining the gels with coomassie blue dye. Comparison of Lanes 2 and 3 in FIG. 5A shows that the global pattern of polypeptides from a filtered (see, Lane 2) versus a non-filtered (see, Lane 3) lysate are indistinguishable. The data demonstrates that, while the filter is highly efficient at removing DNA and reducing lysate viscosity, the filter does not capture a significant proportion of lysate polypeptides. This conclusion is supported by the data of FIGS. 5B and 5C, in which the filtered lysate was subjected to western blot detection of polypeptides that are representative of a specific cellular compartment.

Referring to FIG. 5B, A431 cells were lysed with either RIPA buffer (see, Lane 2) or denaturing buffer (see, Lane 3). The RIPA lysate was mixed with an equal volume of 2× Laemmli buffer and subjected to SDS-PAGE. The denaturing buffer lysate was passed over the filter and mixed with an equal volume of 2× Laemmli buffer and subjected to SDS-PAGE. Western blot analysis was performed and blots were probed with antibodies to detect AIF protein (mitochondrial), Flotillin protein (membrane), and histone H3 (nuclear).

Referring to FIG. 5C, A431 cells were lysed with either RIPA buffer (see, Lane 2) or denaturing buffer (see, Lane 3). The RIPA lysate was mixed with an equal volume of 2× Laemmli buffer and subjected to SDS-PAGE. The denaturing buffer lysate was passed over the filter and mixed with an equal volume of 2× Laemmli buffer and subjected to SDS-PAGE. Western blot analysis was performed and blots were probed with antibodies to detect TFII protein and HSP90 protein, both of which are cytoplasmic. Lane 1 in FIGS. 5A, 5B, and 5C are molecular weight marker lanes.

FIG. 5 B (Lane 3) and FIG. 5C (Lane 3) show that polypeptides representative of mitochondrial, membrane, nuclear and cytoplasmic fractions of the A431 cells were present in the filtered denaturing buffer lysate. Interestingly, when compared to a classical RIPA buffer (e.g., 50 mM Tris-HCl pH 7.5, 150 mM NaCl, 1% IGEPAL, 0.1% SDS, and 0.5% sodium deoxycholate) (see, FIG. 5A—Lane 1, FIG. 5B—Lane 2, and FIG. 5C—Lane 2) the denaturing buffer was superior at extracting total polypeptides, particularly at the lower molecular weights around 16 kD (compare Lanes 2 and 3 in FIG. 5A) and was also clearly superior at extracting nuclear proteins as demonstrated by the lack of histone H3 in the RIPA lysate (see, FIG. 5B, Lane 2) compared to the denaturing buffer lysate (see, FIG. 5B, Lane 3).

When performing immunoprecipitations, it is often desirable to obtain a polypeptide population that is representative of total cellular proteins. In particular, when examining protein post-translational modifications it is important to look at the whole cell proteome including nuclear proteins. It is also true that once nuclear proteins are released from a cell or tissue that the resulting lysate is often highly viscous due to the release of genomic DNA. As genomic DNA and lysate viscosity are known to interfere with immunoprecipitation efficiency (see, Moser et al., Nat. Protoc., 2009, 4, 674-685). Methods have been devised to reduce viscosity that include Benzonase® treatment, multiple passages through a narrow bore syringe, and sonication, but these methods are time consuming and can damage protein samples.

In contrast, the combination of the denaturing buffer and the filter, as described herein, allow highly efficient and rapid processing of lysates to obtain non-viscous, polypeptide rich lysates suitable for many downstream applications, including immunoprecipitations and western blot applications. The combination of the filter and the denaturing lysis buffer has been shown to be superior at extracting nuclear proteins as determined by the more abundant presence of histone H3 in the denaturing buffer sample (see, Lane 3).

Example 6: Polypeptide Recovery of Lysates after Filtering

Figure 6B:
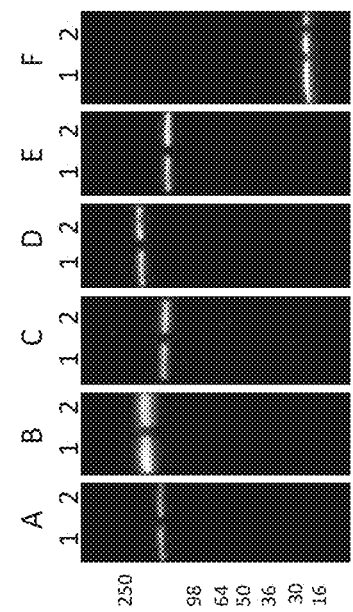
FIGS. 6A and 6B show representative data demonstrating the efficient recovery of lysate polypeptides after viscosity reduction using a filter as described herein.
Figure 6A:
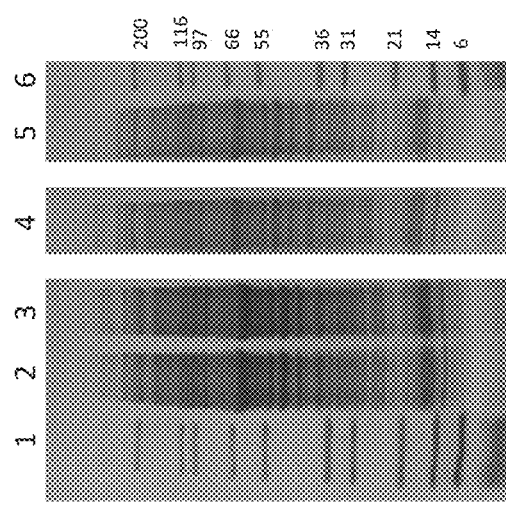

Referring to FIGS. 6A and 6B, representative data demonstrating the efficient recovery of lysate polypeptides after viscosity reduction using the filter is shown. These figures also present data demonstrating the use of the denaturing lysis buffer and comparing the efficiency of lysis between the denaturing lysis buffer described herein and Laemmli buffer. In particular, tissue culture cells were lysed with Laemmli buffer and viscosity was reduced by either multiple passages of the lysate through a narrow gauge needle (see, Lane 2) or by passage through the filter (see, Lane 3). Lysates were produced from tissue culture cells using either Lamelli buffer (see, Lane 4) or denaturing buffer (see, Lane 5). The viscosity in both lysates was reduced by passage through the filter. An equal volume of each lysate was run on SDS-PAGE and proteins were visualized by coomassie blue staining of the gels. Lanes 1 and 6 show molecular weight markers.

FIG. 6A compares the polypeptide profiles generated from a lysate that has been passed through a narrow gauge needle to reduce viscosity (see, Lane 2) compared to a lysate that has been passed over the filter to reduce viscosity. The resulting polypeptides were run on SDS-PAGE and visualized using a coomassie blue protein stain. Comparison of the polypeptide profiles between FIG. 6A Lanes 2 and 3 demonstrate that the filter does not remove a significant amount of polypeptides during lysate clarification. Lanes 4 and 5 (see, FIG. 6A) show polypeptide compositions generated from lysis in Laemmli buffer (see, Lane 4) or in the denaturing buffer (see, Lane 5). After cell lysis of an equal number of cells and passage over the filter, polypeptides were run on SDS-PAGE and visualized by coomassie staining. The lysates generated from Laemmli and the denaturing buffer are indistinguishable.

Referring to FIG. 6B, equal numbers of tissue culture cells were lysed in equal volumes of either denaturing buffer (see, Lane 1) or Laemmli buffer (see, Lane 2). Lysates were run on SDS-PAGE, transferred to PVDF membranes and probed for the following protein targets: A-E-cadhering, B-epidermal growth factor receptor, C-p120, D-TFII-I, E-HK1 and F-histone H3.

Further examination of the efficiency of protein extraction by the denaturing buffer and preservation of a total polypeptide population after passage over the filter are demonstrated in FIG. 6B. This figure shows western blot analysis of lysates generated from Laemmli buffer or from the denaturing buffer after passage over the filter. It can be seen that proteins extracted from the cell membranes (see, blots A, cadherin and B, epidermal growth factor receptor), cytoplasm (blots C, p120 and D, TFII-I) and the nucleus (blots E, HK1 and F, histone H3) are fully represented by both Laemmli buffer and denaturing buffer after passage over the filter. Laemmli buffer is recognized as an extremely stringent buffer that extracts total proteins from cell and tissue samples. FIG. 6B demonstrates that the denaturing buffer is also capable of extracting a protein population comparable to Laemmli buffer.

Example 7: Polypeptide Recovery of Lysates after Filtering

Referring to FIGS. 7A and 7B, representative data demonstrates the recovery of polypeptides from a Laemmli buffer lysate that has been passed over a filter. In particular, referring to FIG. 7A, 16×10$^6$ A431 cells were lysed with 600 µl of Laemmli buffer and filtered (see, Lane 4) or sheared with syringe needle (see, Lane 3). After boiling for 5 minutes, 3% of each sample was loaded on SDS-PAGE and stained with Coomassie Blue. Lane 1 shows protein markers; Lane 2 is empty; Lane 3 shows lysate sample in which viscosity was reduced by passage of lysate multiple times through a syringe; and Lane 4 shows lysate in which viscosity was reduced by a single passage through the filter. In particular, referring to FIG. 7B, 16×10$^6$ A431 cells were lysed with 600 µl of Laemmli buffer and filtered (see, Lane 3) or sheared with syringe needle (see, Lane 2). After boiling for 5 minutes, 3% of each sample was loaded on SDS-PAGE, transferred to a PVDF membrane and probed by anti-EGFR antibody. EGFR is visible at approximately 180 kD.

Comparison of an unfiltered lysate that has been passed through a narrow gauge needle several times to reduce viscosity (see, Lane 3) with filtered lysate (see, Lane 4) demonstrates the superior quality of the polypeptides in the filtered lysate as indicated by protein smearing at high molecular weights (>200 kD) and protein focusing throughout the gel which only occurs in the unfiltered lysate (see, Lane 3). The superior quality of the western blot signal in FIG. 6B, Lane 2 (filtered) compared to Lane 3 (non-filtered) is demonstrated by the smeary signal obtained for EGFR detection in the unfiltered lysate compared to the crisp signal obtained in the filtered lysate lane. Cell lysate preparation in Laemmli buffer followed by western blot analysis of lysates is a common application that should benefit from the speed and ease of the methods, compositions, and kits described herein.

Example 8: Immunoprecipitation of SUMOylated Proteins

Figure 8:
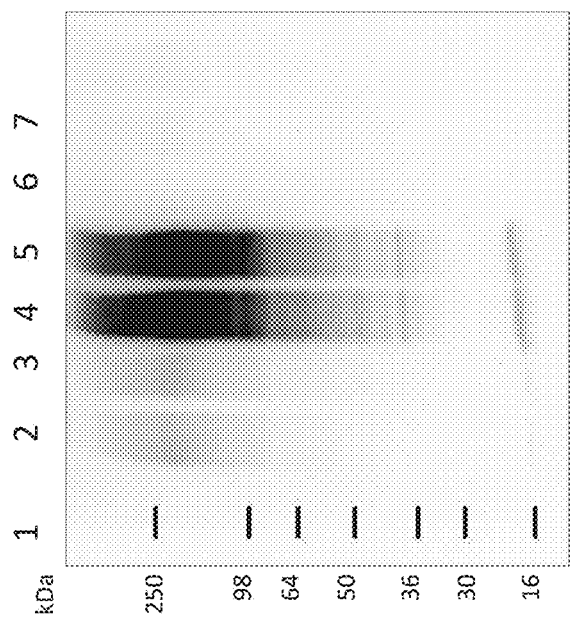
FIG. 8 shows a representative set of data from an immunoprecipitation kit as described herein.

Referring to FIG. 8, data from an immunoprecipitation kit is shown. In particular, a cell lysate was prepared by lysing 16×10$^6$ A431 cells with denaturing lysis buffer. Lysate viscosity was reduced using the filter (see, Lanes 3, 4, and 6) or sheered using passage through a narrow gauge syringe (see, Lanes 2, 5, and 7). 1 mg of lysate was incubated with 30 µl of SUMO-2/3 affinity beads (see, Lanes 4 and 5) or 30 µl of control beads (see, Lanes 6 and 7) at 4° C. for 2 hours and the immuno-precipitated proteins were analyzed by Western Blot. The blot was probed by anti-SUMO-2/3 antibody and SUMOylated proteins were visualized by chemiluminescent detection. SUMOylated proteins were enriched in Lanes 4 and 5, the majority of SUMO signal occurring between molecular weights 80 to >250 kDa. Lane 1 shows molecular weight markers; Lane 2 shows 0.1% input lysate from sheered sample; Lane 3 shows 0.1% input lysate from filtered sample; Lane 4 shows SUMOylated proteins from filtered sample; Lane 5 shows SUMOylated proteins from sheered sample; Lane 6 shows control beads incubated with filtered sample; and Lane 7 shows control beads with sheered sample.

The lysates prepared herein are well suited for detecting protein post-translational modifications (PTMs). This is because the lysis buffer/dilution buffer used herein is denaturing and breaks up protein complexes to allow immuno-precipitation of only modified protein species and the filter allows rapid reduction in viscosity of the lysate which helps maintain the true PTM profile of the lysate. The following steps are performed. Tissue culture cells are treated as required by one skilled in the art. Each immunoprecipitation assay uses about 0.5 to 1.0 mg of lysate protein. The methods provided herein assume that 150 cm$^2$ plates are being processed.

The appropriate volume of lysis buffer and dilution buffer is supplemented with de-ubiquitin/de-SUMOylation inhibitor (10 µl per ml of buffer) and protease inhibitor cocktail (10 µl per ml of buffer). The skilled artisan may use about 5-10× the volume of dilution buffer to lysis buffer. Final volumes will need to be determined by the end-user. The buffers are placed on ice.

PBS pH 7.4 buffer (20 ml of PBS is utilized per tissue culture plate being processed), cell scrapers, and liquid nitrogen will be used (if snap freezing cell lysates for later analysis is desired). Before processing tissue culture cells, it is recommended to label tubes ready for lysate collection.

Tissue culture plate(s) are removed from the incubator and growth media is gently aspirated. Cells are washed two times in 10 ml each of 4° C. PBS buffer at pH 7.4. The PBS is removed by aspiration. After the final PBS wash, the plate is tilted and left for 20-30 seconds to collect residual PBS.

Cells are lysed by adding 300-500 µl of supplemented denaturing lysis buffer to the plate and harvested using a cell scraper. The cell lysate will become viscous during harvesting due to nuclear lysis and release of genomic DNA. Lysate transfer may require a snipped pipette tip.

The lysate is transferred to a 15 ml tube (or similar) on ice. The total lysate volume should not exceed 2× the original lysate volume (e.g., 600 µl final volume for an original lysis volume of 300 µl). The lysate is diluted with 5-10× volume of dilution buffer. The lysate is passed through the syringe filter under compression and the filtrate (filtered lysate) is collected into a fresh tube and placed on ice.

Upon quantification, a protein concentration between 0.5-1.2 mg/ml indicates that there is sufficient protein in one 150 cm$^2$ plate to carry out 1-2 immunoprecipitations. Lysates that will not be used immediately for further analysis can be aliquoted and snap frozen in liquid nitrogen and stored at −70 to −80° C. Lysates should be stable for several months. FIG. 8 shows results from the methods of a kit described herein. In this example, the PTM detected is SUMOylation. Lane 4 shows the results of a SUMOylation enrichment utilizing the buffers and the filter. For comparison, Lane 5 shows results using the buffers with lysate viscosity reduction performed by passage through a narrow gauge needle. Comparison of lanes 4 and 5 show that the resulting IP data is very similar Utilizing the buffers and filters described herein creates a far simpler and less tedious method of lysate preparation.

In other iterations of the kit, any PTM can be detected using the methods described herein, including ubiquitination, acetylation, phosphorylation, and methylation.

Example 9: Representative Polyurethane Filter Properties

FIG. 9 shows a table including several representative properties of the filters described herein. Filters having a range of values for the properties given in the table were tested for conformity to the following specifications: 1) the ability to reduce the viscosity of cell lysates containing approximately 50 µg/ml and 100 µg/ml of un-sheared genomic DNA by >90%; and 2) generation of a filtered lysate that contains >90% of the original lysate polypeptide population. The specifications were used to determine a working range and suitable value for the filter.

Example 10: Detection of PD-L1 Ubiquitination in Response to EGF Stimulation

Figure 10:
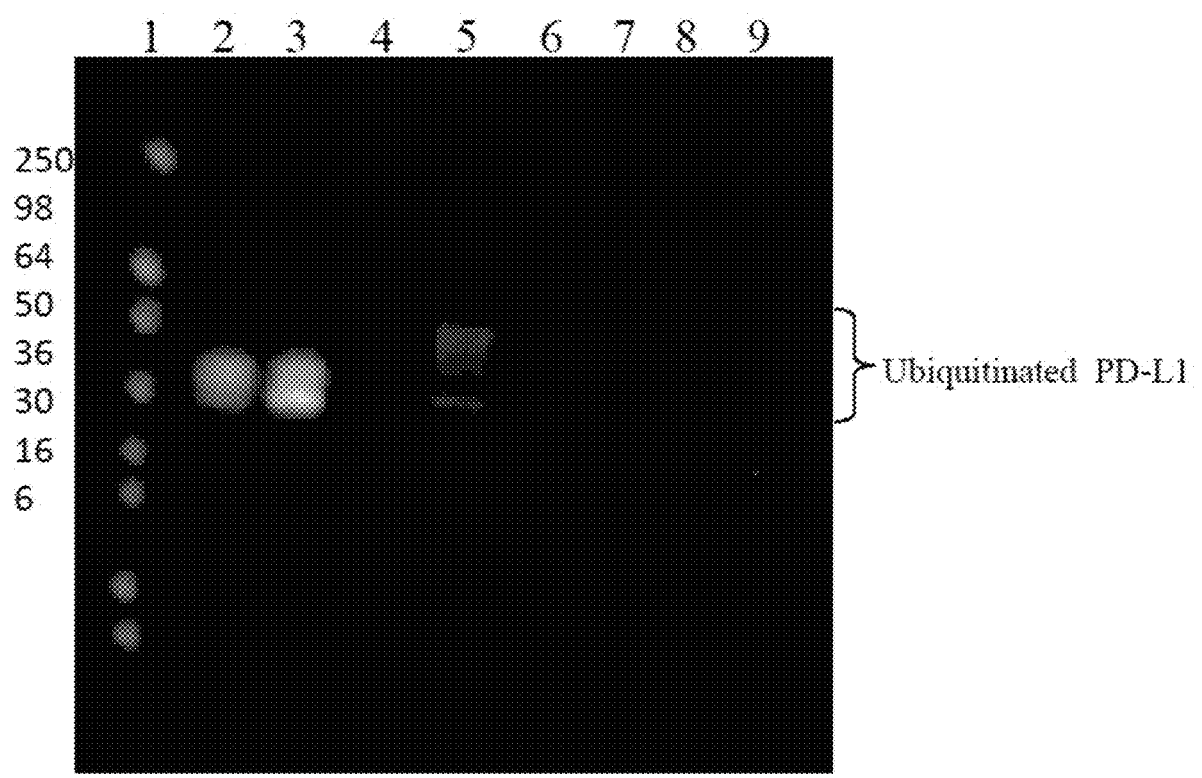
FIG. 10 shows results of detection of (programmed death ligand 1) PD-L1 ubiquitination in response to epidermal growth factor (EGF) stimulation.

Referring to FIG. 10, A431 cells were either treated (lanes 3, 5, 7, and 8) or untreated (lanes 2, 4, 6, and 9) with epidermal growth factor (EGF) for one hour at 37° C./5% $CO_2$. Cells were lysed using the lysis buffer and lysate viscocity was reduced using the filter described herein. Lysate (1 mg per sample) was immunoprecipitated (IP) with ubiquitin affinity beads (lanes 4, 5, 6, and 7) in the presence (lanes 4 and 5) or absence (lanes 6 and 7) of the de-ubiquitin inhibitor NEM (N-ethylmaleimide). The data shows that PD-L1 ubiquitination is greatly enhanced upon EGF stimulation (compare lane 4 (minus EGF) with lane 5 (plus EGF)). Specificity of the ubiquitin signal was demonstrated by the fact that the signal was greatly reduced in the absence of de-ubiquitin inhibitor (compare lane 5 (EGF stimulation plus NEM) with lane 7 (EGF stimulation minus NEM)). Lanes 2 and 3 showed PD-L1 input signal (1% of IP input) running at around 50 kD. Lane 8 represents signal from control beads (beads that do not have ubiquitin affinity domains attached) plus 1 mg of EGF treated lysate and lane 9 represents ubiquitin affinity beads minus lysate. The absence of signal in lanes 8 and 9 serves to further demonstrate the specificity of the ubiquitinated PD-L1 signal in the EGF treated cell lane (lane 5). The PD-L1 antibody was obtained from Cell Signaling Technology, Cat #13684. The primary antibody dilution was 1:1,000 in TBST, and the secondary antibody was HRP conjugated anti-rabbit at a 1:10,000 dilution.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for reducing the viscosity of a cell lysate or tissue lysate consisting of:
    contacting the cell lysate or tissue lysate with a compressible and open-cell foam filter having a pore size from about 0.65 mm to about 1.22 mm, a density from about 1.3 lbs/ft$^3$ to about 3.0 lbs/ft$^3$, and an indentation load deflection (ILD) from about 60 ILD to about 90 ILD, wherein the filter is present in a syringe;
    compressing the filter to recover the lysate absorbed in the filter, wherein the compression ratio is from about 50% to about 95%; and
    collecting the filtered lysate, wherein the filtered lysate contains at least 95% of the polypeptides in the original cell lysate or original tissue lysate, and wherein the filtered lysate contains no more than 10% of the genomic DNA in the original cell lysate or original tissue lysate.

2. The method of claim 1, wherein the compressible and open-cell foam filter is a polyurethane foam.

3. The method of claim 1, wherein the ratio of the volume of the lysate to filter is from 0.1 to 4, from 0.1 to 2, or from 1 to 2.

4. The method of claim 1, wherein the volume of the lysate is from 0.1 ml to 1,000 ml, from 0.5 ml to 500 ml, from 1 ml to 200 ml, or from 1 ml to 100 ml.

5. The method of claim 1, further comprising diluting the filtered lysate with 1×-10× volume, 3×-10× volume, or 5×-10× volume of dilution buffer to produce a diluted filtered lysate.

6. The method of claim 5, wherein the dilution buffer comprises a detergent, a salt, and a protease inhibitor.

7. The method of claim 1, wherein the unfiltered lysate is generated by a method comprising:
    separating growth media from the cells or tissue;

washing the cells or tissue with wash buffer;
removing the buffer from the cells or tissue;
lysing the cells or tissue by adding lysis buffer, wherein the lysate comprises at least 90% of polypeptides and genomic DNA extracted from the cells or tissue, and wherein the genomic DNA is not sheared;
transferring the lysate having an original lysate volume to a container; and
diluting the lysate with dilution buffer to produce a diluted lysate volume.

8. The method of claim 7, wherein the lysis buffer comprises a post-translational modification inhibitor cocktail that comprises one or more of a de-ubiquitin inhibitor, a phosphotyrosine inhibitor, a de-SUMOylation inhibitor, a phosphoserine inhibitor, a phosphothreonine inhibitor, a de-acetylase inhibitor, and de-methylase inhibitor.

9. A method for detecting ubiquitinated programmed death ligand 1 (PD-L1) comprising:
contacting a cell lysate or tissue lysate containing or suspected of containing ubiquitinated PD-L1 with a compressible and open-cell foam filter having a pore size from about 0.65 mm to about 1.22 mm, a density from about 1.3 lbs/ft3 to about 3.0 lbs/ft3, and an indentation load deflection (ILD) from about 60 ILD to about 90 ILD, wherein the filter is present in a syringe;
compressing the filter to recover the lysate absorbed in the filter, wherein the compression ratio is from about 50% to about 95%;
collecting the filtered lysate, wherein the filtered lysate contains at least 95% of the polypeptides in the original cell lysate or original tissue lysate, and wherein the filtered lysate contains no more than 10% of the genomic DNA in the original cell lysate or original tissue lysate; and
detecting the presence or absence of ubiquitinated PD-L1 by contacting the filtered lysate with an anti-ubiquitin agent and an anti-PD-L1 agent.

10. The method of claim 9, wherein the anti-ubiquitin agent is an anti-ubiquitin antibody or ubiquitin affinity beads.

11. The method of claim 9, wherein the anti-PD-L1 agent is an anti-PD-L1 antibody.

12. The method of claim 9, wherein the filtered lysate is contacted first with the anti-ubiquitin agent to immunoprecipitate ubiquitinated proteins, and then the ubiquitinated proteins are contacted by the anti-PD-L1 agent to detect ubiquitinated PD-L1.

13. The method of claim 9, wherein the ratio of the volume of the lysate to filter is from 0.1 to 4, from 0.1 to 2, or from 1 to 2.

14. The method of claim 9, wherein the volume of the lysate is from 0.1 ml to 1,000 ml, from 0.5 ml to 500 ml, from 1 ml to 200 ml, or from 1 ml to 100 ml.

15. The method of claim 9, wherein the unfiltered lysate is generated by a method comprising:
separating growth media from the cells or tissue;
washing the cells or tissue with wash buffer;
removing the buffer from the cells or tissue;
lysing the cells or tissue by adding lysis buffer, wherein the lysate comprises at least 90% of polypeptides and genomic DNA extracted from the cells or tissue, and wherein the genomic DNA is not sheared;
transferring the lysate having an original lysate volume to a container; and
diluting the lysate with dilution buffer to produce a diluted lysate volume.

* * * * *